United States Patent [19]

Belagaje et al.

[11] Patent Number: 4,710,464
[45] Date of Patent: Dec. 1, 1987

[54] TRANSCRIPTION TERMINATORS

[75] Inventors: Ramamoorthy Belagaje; Stuart A. Kuhstoss; R. Nagaraja Rao, all of Indianapolis, Ind.

[73] Assignee: Eli Lilly and Company, Indianapolis, Ind.

[21] Appl. No.: 655,184

[22] Filed: Sep. 27, 1984

[51] Int. Cl.$^4$ .................. C12P 19/34; C12P 21/00; C12N 15/00; C12N 1/00; C12N 1/20; C12N 1/16; C12N 1/18; C07H 21/04

[52] U.S. Cl. .................. 435/91; 435/68; 435/172.1; 435/172.3; 435/243; 435/253; 435/255; 435/256; 435/320; 536/27

[58] Field of Search .................. 435/68, 70, 71, 91, 435/172.3, 172.1, 240, 243, 253, 255, 256, 317; 536/27; 935/6, 8, 29, 34, 38, 36, 39, 66–75

[56] References Cited

U.S. PATENT DOCUMENTS 4,513,086  4/1985  Fayerman et al. .................. 435/91

OTHER PUBLICATIONS

Rosenberg et al., "Regulatory Sequences Involved in The Promotion and Termination of RNA Transcription", Ann. Rev. Genet. 13: 319 (1979).
Holmes, W. M. et al., 1983, *Cell 32:* 1029–1032.
Brennan and Geiduschek, 1983 *Nucleic Acids Research 11:* 4157–4175.
Russell and Bennett, 1982, *Gene 20:* 231–243.
Rosenberg, M. et al., 1983, *Science 222:* 734–739.
Das, et al., 1976, *Proc. Natl. Acad. Sci. 78:* 1959–1963.
Stueber and Bujard, 1982, *EMBO Journal 1:* 1399–1404.
Gentz, R. et al., 1981, *Proc. Natl. Acad. Sci. 78:* 4936–4940.
Beck, E. et al., 1981, *Gene 19:* 327–336.
Kuhstoss and Rao, 1983, *Gene 26:* 295–299.
Richardson, M. et al., 1982, *Gene 20:* 451–457.

*Primary Examiner*—James Martinell, Ph.D.
*Attorney, Agent, or Firm*—Mark R. Daniel; Leroy Whitaker

[57] ABSTRACT

The present transcription terminators are DNA sequences characterized by their ability to terminate the transcription of DNA sequences. The present sequences are portable, have a variety of restriction endonuclease sites and are useful in controlling the expression in hosts of DNA sequences coding for prokaryotic, eukaryotic and viral proteins and polypeptides.

22 Claims, 7 Drawing Figures

Restriction Site Map of
Plasmid pKC326
(9.7kb)

Restriction Site Map of
Plasmid pKC345
(10.8kb)

Restriction Site Map of
Plasmid pKC354
(12.5kb)

Restriction Site Map of
Plasmid pKC356
(11kb)

TRANSCRIPTION TERMINATORS

TECHNICAL FIELD OF INVENTION

This invention relates to DNA sequences that are characterized by the ability to terminate the transcription of DNA sequences. These transcription terminators are further characterized in that they are portable and contain a variety of restriction endonuclease sites. As will be appreciated from the disclosure to follow, these DNA sequences, and particularly recombinant DNA molecules containing them, may be used to improve the production of various polypeptides in host cells transformed with DNA sequences coding for those polypeptides.

BACKGROUND ART

Methods for producing polypeptides by host organisms transformed with recombinant DNA molecules are well known (for a general review, see the Feb. 11, 1983 issue of Science, 219:535 entitled "Biotechnology"). Such recombinant production methods generally comprise preparing a DNA sequence encoding a polypeptide of interest, inserting it into an expression vehicle (e.g. a virus or a plasmid) to produce a recombinant DNA molecule in which the DNA sequence is under the control of an expression control sequence, transforming a suitable host organism with the recombinant DNA molecule, and culturing the host to produce the polypeptide of interest.

The level of recombinant production of polypeptides in a host cell is governed by four major factors: (1) the number of copies of the DNA sequence encoding the polypeptide, (2) the efficiency with which those DNA sequences are transcribed to messenger RNA ("mRNA"), (3) the efficiency with which the mRNA is translated to polypeptides, and (4) the stability of the polypeptides in the host cell. Transcription and translation together comprise expression of a DNA sequence. Efficiency of transcription in turn is dependent upon, inter alia, various sequences such as, for example, promoters and effector binding sites that serve as loci to initiate mRNA synthesis. Transcription terminator sequences ("transcription terminators") are stop sites for RNA polymerase which halt or regulate transcription. Transcriptional regulation is achieved by modulating the efficiency with which the RNA polymerase can recognize and interact with a given DNA sequence to initiate or to terminate RNA transcription (Rosenberg and Court, 1979, Ann. Rev. Genet. 13:319). For example, such interaction of promoter and terminator regions may be observed in the transcriptional regions of some *E. coli* plasmids where transcription terminators appear to balance transcription initiated by promoters of different strengths (Stüber and Bujard, 1981, Proc. Natl. Acad. Sci. USA 78:167).

This interaction of promotion and transcription termination has also been observed in the cloning of very strong promoters. For example, although strong promoters are desirable for increasing the expression level of a DNA sequence, such promoters may interfere with replication of plasmids containing them. Stable plasmids containing strong promoters from bacteriophage T5 have been constructed using natural transcription terminators downstream from the strong promoters. In the absence of such terminators, it had not been possible to clone these strong T5 promoters (Gentz et al., 1981, Proc. Natl. Acad. Sci. USA 78:4936). Finally, transcription termination may be useful in avoiding the potential disadvantages of the expression or control of a particular gene sequence by "read-through" transcription from promoters in other regions of the expression vector.

Several natural transcription terminators are known. They are divided generally into two classes, independent, and factor-dependent transcription terminators (Holmes et al., 1983, Cell 32:1029. Independent transcription terminators may function independently of other products as stop sites for RNA polymerase. In vivo independent transcription terminators are usually located at the ends, within and between the genes of operons. For example, independent transcription terminators are found near the beginning of biosynthetic operons that are regulated by attenuation, such as the trp operon (Holmes et al., supra). As attenuators, independent terminators regulate expression of downstream cistrons. Independent terminators have also been found to control other types of transcriptional units. Although most independent transcription terminators function only in a single orientation, some bidirectional transcription terminators are also known to exist (Holmes et al., supra).

Generally, independent transcription terminator regions are structurally similar. For example, most terminators include a GC-rich sequence preceding the termination site and a sequence of T-residues in the nontemplate DNA strand attached to the termination site. The RNA polymerase traverses the GC-rich sequence to produce mRNA which can form a stable base-paired stem-and-loop structure within the mRNA. Transcription then usually terminates just downstream from the stem-and-loop structure where the T-residues result in a RNA ending with a sequence primarily comprising uridylate residues (Rosenberg and Court, supra; Holmes et al., supra; and Brennan and Geiduschek, 1983, Nucl. Acids Res. 11:4157).

Although these regions of independent transcription termination have certain similarities, it is extremely difficult, if not impossible, to predict from DNA sequence information alone which regions of DNA will be recognized by RNA polymerase as a transcription terminator. Neither is it yet understood how nucleotide similarities observed at the primary sequence level contribute to specifying a transcription termination function (Rosenberg and Court, supra).

The second general class of transcription terminators is the factor-dependent terminators. Factor-dependent terminators require ancillary products or factors to function as stop sites for RNA polymerase. Factor-dependent terminators comprise a large and diverse group of DNA sequences that are very complex in structure and function (Holmes et al., supra).

DISCLOSURE OF THE INVENTION

The present invention overcomes the problems referred to above by providing a synthetic DNA sequence that is useful as a portable transcription terminator. This sequence comprises a DNA sequence that is both capable of forming a stable stem-and-loop structure when transcribed into mRNA and capable of terminating transcription. It also contains at least two, and preferably several, endonuclease recognition sites which enable the transcription terminator to be used in a variety of recombinant DNA constructions and manipulations.

The present invention also provides methods for using this portable transcription terminator in recombinant DNA molecules to regulate the transcription of DNA sequences that code for a desired polypeptide. It is also an object of this invention to use this portable transcription terminator to allow the cloning of strong promoters and for use in expressing DNA sequences that code for a desired polypeptide. It is a further object of this invention to use this portable transcription terminator to prevent the potential disadvantages of "read-through" transcription of polypeptide encoding DNA from other promoters and control elements in an expression vehicle. Accordingly, as will be appreciated from the description to follow, the DNA sequences and methods of this invention enable more efficient cloning and expression of prokaryotic, eukaryotic and viral polypeptides in a variety of host cells.

BEST MODE OF CARRYING OUT THE INVENTION

Figure 1:
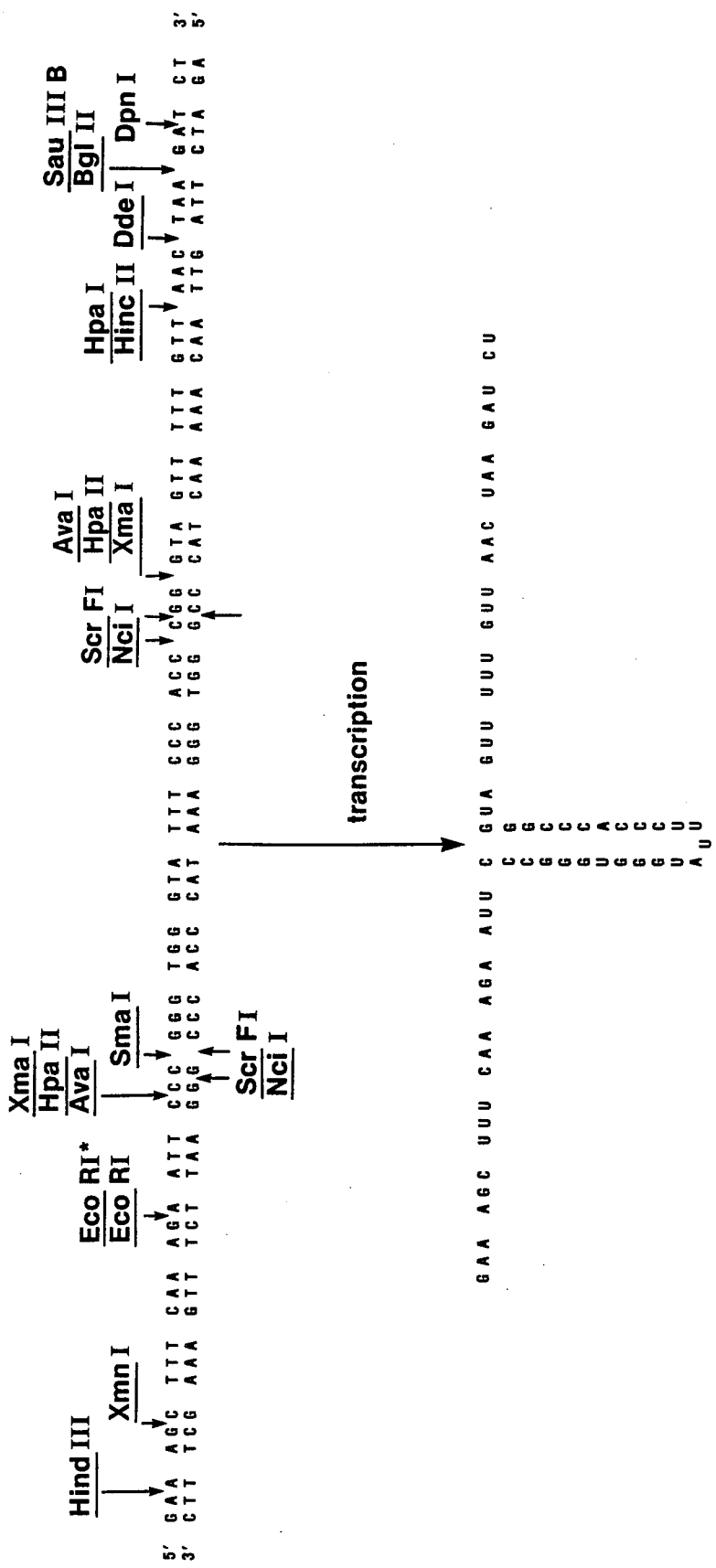
FIG. 1 depicts the DNA sequence of one embodiment of a portable transcription terminator of this invention. It also depicts the various restriction sites in this sequence and the GC-rich stem formed on transcription into RNA.

In order that the invention herein described may be more fully understood, the following detailed description is set forth.

MATERIALS AND METHODS

1. Hosts

Any of a wide number of well known host cells may be used in accordance with the transcription terminators of this invention without departing from its scope. These hosts include, for example, the host cells commonly employed in recombinant DNA expression of desired products. For example, strains of *E. coli, B. subtilis* and other bacteria, yeast and other fungi, and tissue cultures of animal and plant cells, including algae, may be usefully employed.

The selection of a particular host may be done by one skilled in the art without departing from the scope of this invention. In selecting a host, consideration should be given to such factors as compatibility with the expression vector chosen for the transformation (in particular with regard to the origin of replication), toxicity of the polypeptides to be produced to the host, ease of fermentation and product recovery, and costs.

The preferred hosts are *Escherichia coli* and *Streptomyces ambofaciens*.

2. Expression Vectors

Any of a wide number of well known expression vectors may be used in accordance with the transcription terminators of this invention without departing from its scope. For example, these expression vectors include those characterized by expression control sequences selected from the group consisting of trp, lac, lpp, phage λ such as pL and $p_R$, TAC, β-lactamase, *Bacillus veg*, Staphylococcus nuclease, and other sequences that control the expression of prokaryotic, eukaryotic and viral polypeptides, and combinations of these. The vectors may be constitutive or controllable. The particular expression vector should be for compatibility with the chosen host, particularly with regard to the origin of replication and also with regard to the proper functioning of the various control elements involved in the expression of the cloned gene. The vector also should be chosen for compatability with the DNA sequence desired to be expressed. In addition, it should include restriction sites that permit the DNA sequences of the portable transcription terminator of this invention to be inserted therein downstream, and, if desired, upstream of the DNA sequence desired to be expressed.

3. Proteins and Polypeptides

The transcription terminators of this invention are useful in enhancing the production of any prokaryotic, eukaryotic or viral protein or polypeptide. Such products include, for example, human proinsulin, human insulin A-chain, human insulin B-chain, the various interferons, human growth hormone, bovine growth hormone, porcine growth hormone, human blood enzymes such as Factors VIII, IX, urokinase and tissue plasminogen activator, erythropoietin, various antibodies, various viral antigens such as malarial antigens and FMDV antigens, enzymes that catalyze reactions in metabolic pathways and any other polypeptides of interest.

4. DNA Methods and Materials

The recombinant DNA methodology and materials useful in constructing recombinant DNA molecules characterized by the transcription terminators of this invention are conventional. They include the following:

Enzyme Buffers

PstI—150 mM NaCl, 10 mM Tris (pH 7.9), 10 mM $MgCl_2$, 10 mM DTT;
EcoRI—100 mM Tris (pH 7.5), 50 mM NaCl, 10 mM $MgCl_2$;
BglII—60 mM NaCl, 10 mM Tris (pH 7.5), 10 mM $MgCl_2$, 10 mM DTT;
HindIII—Same as Bgl II;
SmaI—20 mM KCl, 10 mM Tris (pH 8.0), 10 mM $MgCl_2$, 10 mM DTT;
Pvu II—Same as Bgl II;
AhaIII—75 mM NaCl, 10 mM Tris (pH 8.0), 10 mM $MgCl_2$, 10 mM DTT;
BamHI—150 mM NaCl, 10 mM Tris (pH 7.9), 10 mM $MgCl_2$;
T4 DNA ligase buffer—50 mM Tris (pH 8.0), 10 mM $MgCl_2$, 20 mM DTT, 1 mM ATP;
10×IBI BAP buffer—0.5M Tris (pH 8.0), 0.5M NaCl.

Plates and Media

TYAp100—TY plates or TY broth containing ampicillin at a concentration of 100 μg/ml;
TYAp100Nm25—TYAp100 plates or broth also containing neomycin at a concentration of 25 μg/ml;
R2 Plates—10.3% sucrose, 0.025% $K_2SO_4$, 1% glucose, 0.2% L-asparagine, 0.01% casamino acids, 0.025M TES (pH 7.2), 0.02M $CaCl_2$, 0.005% $KH_2PO_4$, 50 mM $MgCl_2$, 2.2% agar and trace elements (per liter: 40 mg $ZnCl_2$, 200 mg $FeCl_3.6\ H_2O$, 10 mg $CuCl_2.2$ $H_2O$, 10 mg $MnCl_2.4\ H_2O$, 10 mg $Na_2B_4O_7.10\ H_2O$ and 10 mg $(NH_4)_6\ Mo_{24}.4\ H_2O$);

R2 Overlays—10.3% sucrose, 50 mM $MgCl_2$, 20 mM $CaCl_2$, 0.025M TES (pH 7.2) and 0.41% agar;

P Medium—10.3% sucrose, 0.025% $K_2SO_4$, 0.203% $MgCl_2$, 0.005% $KH_2PO_4$, 0.025M TES (pH 7.2) and $CaCl_2$(0.278%).

LB Medium—10 g Bacto-tryptone, 5 g Bacto-yeast extract and 10 g NaCl per liter.

Kieser Mini-Prep of DNA

We took 5 ml of cells, pelleted them in a table-top centrifuge, removed the supernatant and suspended the pellet in 500 µl 25 mM Tris buffer (pH 8.0) containing 25 mM EDTA. We then added 250 µl of 0.3N NaOH and 2% SDS and mixed the sample on a Vortex mixer. We placed the mixture at 70° for 10 min and then cooled it to room temperature. We added 80 µl phenol:$CHCl_3$ (1:1) to the mixture, mixed well on the Vortex, and centrifuged for 5 min. We removed the upper layer and put the contents into a new eppendorf tube. We added 70 µl of 3M sodium acetate to the tube, filled the tube with isopropanol at room temperature and let it stand for 5 min. at room temperature. We centrifuged the sample for 5 min., removed the supernatant and then centrifuged the material again briefly to remove the residual liquid. We dissolved the pellet in 500 µl TE, added 25 µl of 100 mM spermine.HCl and let this stand for 5 min. at room temperature. We then centrifuged the sample for 5 min., removed the supernatant and suspended the pellet in 300 µl of 0.3M sodium acetate, 0.01M $MgCl_2$ solution. We added 700 µl of cold ethanol, let it stand for 5 min. at room temperature and centrifuged the sample for 5 min., removed the supernatant, washed the pellet with ethanol and dried it.

Ethanol Precipitation

We added 1/10 vol. of 3M sodium acetate (e.g. 5 µl NaOAc) to about 50 µl of the DNA solution. We then added 3 vol. of ethanol (e.g. 150 µl), chilled the solution in a dry ice-isopropanol bath and centrifuged the solution for 5 minutes in an eppendorf microcentrifuge. We then removed the supernatant, washed the pellet with ethanol and dried it.

Preparation and Transformation of Competent *E. coli*

Competent *E. coli* were prepared and transformed according to the method of Maniatis et al., 1982, Cloning: A Laboratory Manual, Cold Spring Harbor Laboratory, Cold Spring Harbor, N.Y.

Preparation and Transformation of Streptomyces Protoplasts

Streptomyces protoplasts were prepared by growing the cells for 48–60 hours at 30° C. in YEME+34% sucrose, 5mM $MgCl_2$ and 0.5% glycine. The mycelium was recovered by centrifugation (800 g for 10 minutes in a bench top centrifuge) and washed twice in 10.3% sucrose. The mycelium from 25–50 ml of culture was suspended in 3–4 ml of L medium and incubated for 1 hour at 32° C. During this interval the suspension was pipetted up and down once or twice to disperse clumps. Five ml of P medium were added, and the suspension was then filtered through a plug of cotton wool. The protoplasts were recovered by centrifugation (800 g for 10 minutes) and washed twice with 5 ml of P medium. The protoplasts were then suspended in 4 ml of P medium and the number of protoplasts determined microscopically using a hemocytometer slide. If the protoplasts were not to be used immediately, the suspension was divided into aliquots (about 1 ml) containing $5 \times 10^9$–$10^{10}$ protoplasts in sterile polypropylene screw-cap tubes. The suspensions were frozen slowly by placing the tubes in a container of ice, which was in turn placed at −70° C. The protoplasts were stored at this temperature until needed, at which time the frozen suspension was thawed rapidly by immersion in a 37° C. water bath.

Streptomyces protoplasts were transformed by adding 0.4 ml of P medium to a tube containing Streptomyces protoplasts in 200 µl of buffer. We then added a 200 µl aliquot of this mixture to the transforming DNA, along with 0.5 ml of 55% polyethylene glycol (PEG) in P medium mixed the contents and allowed them to stand 1 minute at room temperature. We then added an appropriate volume (usually about 10–100 µl) of these protoplasts to 3 ml of R2 overlay and poured the contents onto an R2 plate, tilting the plate to spread the agar. We allowed the medium to set up and then incubated it overnight at 30° C.

For drug selection experiments, we added the drug to 3 ml of R2 overlay, using enough of the drug so that the final concentration was as indicated (i.e., we estimate the volume of the plate and the overlays; we assumed 40 ml as the final volume). The day after the host cells were transformed we poured the R2 overlay the regeneration plates and continued incubation at 30° C.

5. Fermentation and Purification of Proteins and Polypeptides

The fermentation and purification procedures useful to culture hosts characterized by the transcription terminator of this invention are also conventional and well known in the art. The selection of a particular fermentation procedure or purification scheme will depend on the host, the level of expression, the particular protein produced, protein stability and the various impurities also present in the culture broth.

6. The Transcription Terminators Of This Invention

As we have previously stated, the portable transcription terminators of this invention are useful for enhancing the expression of DNA sequences coding for desired polypeptides in hosts transformed with those DNA sequences. They are also useful in methods for cloning and selecting strong promoters for subsequent use in the expression of DNA sequences.

When the transcription terminators of this invention are used to enhance the expression of a selected DNA sequence, they are inserted into a recombinant DNA molecule downstream of the translational stop codon of that DNA sequence. The distance is sufficient so as not to interfere with transcription of the DNA sequence and yet near enough to prevent read through to other sequences not desired to be transcribed. This distance may be about 10–20 bp downstream of the stop codon but may vary depending upon the particular recombinant DNA molecule. In that location, the terminators function to stop transcription after the desired DNA sequence has been transcribed into mRNA.

More preferably, a second transcription terminator is also inserted into the recombinant DNA molecule carrying the selected DNA sequence at a location upstream of the promoter and effector binding sites controlling the expression of that DNA sequence. The second transcription terminator is inserted upstream far enough to stop other promoters from reading through the region comprising the expression control sequences and the DNA sequence of interest without interfering with the functioning of the expression control sequences. This distance may be about 10–20 bp upstream from the expression control sequences but may vary depending upon the particular recombinant DNA molecule. In this preferred embodiment of the invention "readthrough" transcription from other promoters and elements in the recombinant DNA molecule is substantially prevented. It should be understood that either upstream or downstream, one or more of the transcription terminators of this invention may be combined and used together to enhance the expression of the desired DNA sequence by protecting it from readthrough and by efficiently terminating transcription of the desired DNA sequence.

In the embodiment of this invention where the transcription terminator is employed to select strong promoters for subsequent use in expressing DNA sequences that code for a desired polypeptide, the terminator is inserted downstream of the site in the cloning vehicle into which the promoter sequence will be cloned. In that location, the terminator should also be downstream of the DNA sequence that codes for the product used to evaluate the strength of the chosen promoter. Again, in a preferred embodiment, a second terminator is inserted upstream of the site in the cloning vehicle into which the promoter sequence will be cloned. At that location the terminator functions to avoid the effect of any "readthrough" transcription from other promoters to insure that the cloned promoter's effect is evaluated independently of other promoters in the cloning vehicle.

In order that this invention may be more fully understood, the following examples are provided.

EXAMPLE 1

This example illustrates the synthesis of a portable transcription terminator of this invention. We prepared a portable transcription terminator containing at least ten restriction endonuclease sites as follows:

We chemically synthesized the following four oligonucleotide sequences either on a Biosearch Sam I or ABS 380A DNA synthesizer (Applied Biosystems Inc., 850 Lincoln Center Dr., Foster City, CA 94404), following the procedures recommended by the manufacturers:

Sequence 1:
dGAAAGCTTTCAAAGAATTCCCGGGTGGGTATTT
Sequence 2: dCCCGGGTAGTTTTTG
Sequence 3: dAGATCTTAGTTAACAAAAAC
Sequence 4: dTACCCGGGTGGGAAATACCC wherein A is deoxyodenyl
G is deoxyguanyl,
C is deoxycytosyl and
T is thymidyl.

Many other DNA synthesizing machines are known in the art and can be used to conventionally prepare the above sequences. In addition, the oligonucleotides can be synthesized in accordance with the known procedures of Itakura et al., 1977, Science 198:1056 and Crea et al., 1978, Proc. Nat. Acad. Sci. USA 75:5765.

The portable transcription terminator of this invention was prepared from the four oligonucleotides by a two step process:

(a) We labelled sequences 3 and 4 with $^{32}$P and then ligated sequences 3, 4 and unphosphorylated sequence 2 with T4 DNA ligase under standard conditions. The single strands were separated by polyacrylamide gel (15%) electrophoresis and the following sequence was isolated:

Sequence 5:

dAGATCTTAGTTAACAAAAA

CTACCCGGGTGGGAAATACCC (b) We then annealed $^{32}$P labelled sequences 1 and 5 in Klenow buffer* and, after reacting with Klenow enzyme, the final 65 bp synthetic portable transcription terminator shown below was produced.

5' GAAAGCTTTCAAAGAATTCCCGGGTGGGTATT-
3' CTTTCGAAAGTTTCTTAAGGGCCCACCCATAA-

TCCCACCCGGGTAGTTTTTGTTAACTAAGATCT 3'
AGGGTGGGCCCATCAAAAACAATTGATTCTAGA 5'

The above fragment was conventionally isolated by 15% polyacrylamide gel electophoresis. We confirmed the DNA sequence of this transcription terminator by the method of Messing, 1983, Meth. Enz. 101:20.
*Klenow buffer was prepared with the following composition:
60 mM NaCl
6.6 mM MgCl$_2$
10 mM Tris-Hcl, pH 7.8
6 mM β-mercaptoethanol
500 μM of each of the 4 dNTPs Referring now to FIG. 1, we have depicted both strands of this 65 base pair DNA sequence. We have also depicted the location of the various restriction sites present in that sequence. Finally, we have depicted the GC-rich stem that may be formed on transcription of this DNA sequence into mRNA. This stem and loop structure is formed by pairing residues 19–28 with residues 34–43. Such base pairing is calculated to require −17.8 kcal of free energy. The stem is followed by a string of 5 U residues. From FIG. 1 it should also be observed that restriction of the DNA sequence with Sma I removes the stem and loop structure. This destroys the terminator function of the sequence but retains, unaffected, its secondary function as a multirestriction site carrier.

EXAMPLE 2

In this example, we describe cloning the synthetic terminator produced in Example 1. Such cloning simplifies subsequent manipulation of the terminator and its use in expression vectors. It also provides a convenient system in which to replicate the terminator in order to produce it in a host transformed with the vector, thereby avoiding further synthetic preparation.

Figure 2:
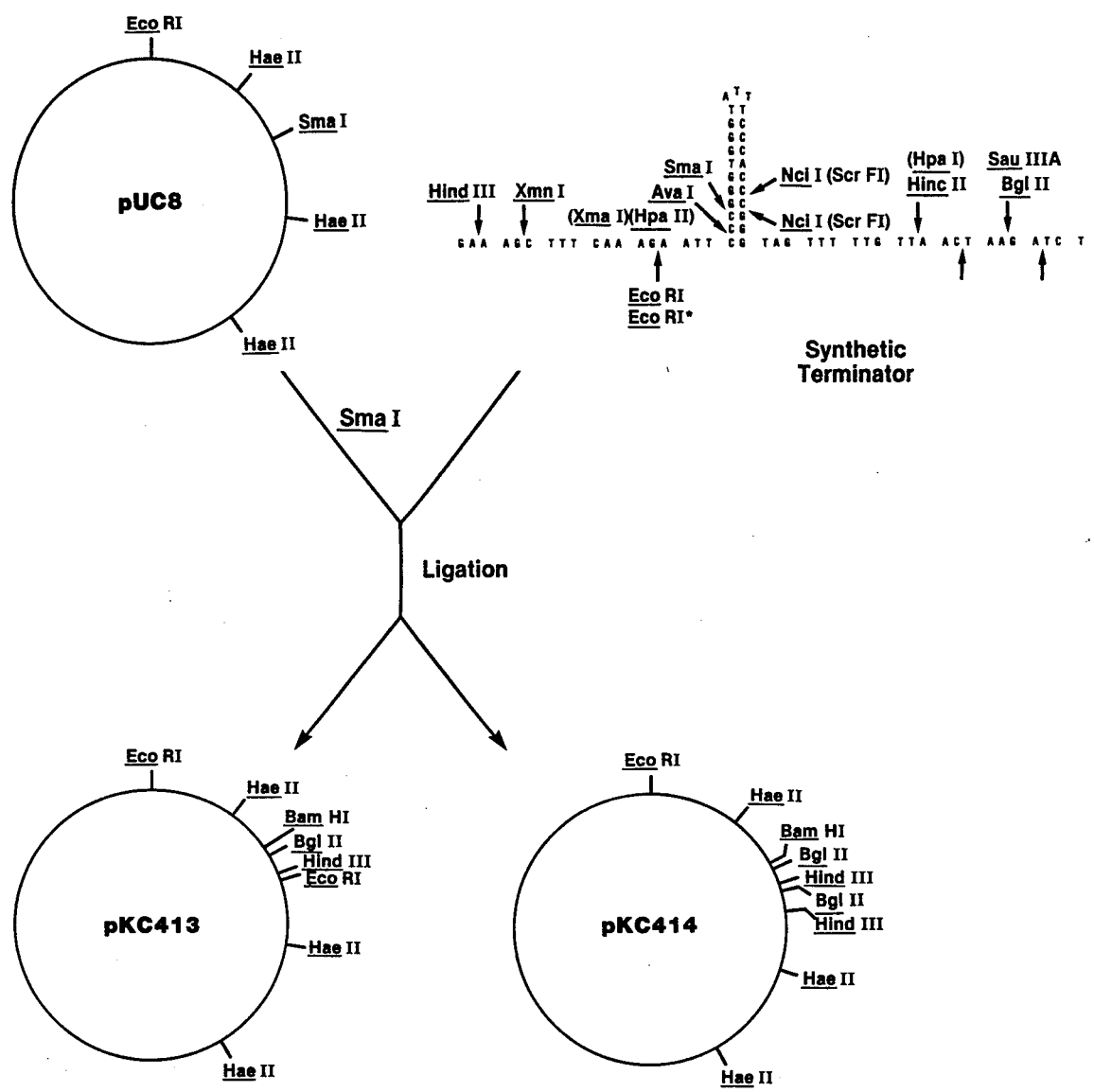
FIG. 2 is a schematic depiction of the construction of expression vectors comprising portable transcription terminators of this invention.

Referring now to FIG. 2, we cloned the portable double stranded transcription terminator of Example 1 into plasmid pUC8 (commercially available from BRL and constructed in accordance with Vieira and Messing, 1982, Gene 19:259. We digested approximately 3 μg of pUC8 with 10 units of SmaI at 37° C. for 1 hour in 10 μl of buffer. We added 40 μl of H$_2$O to the solution and extracted it once with chloroform:isoamyl alcohol (24:1). We then precipitated the DNA with ethanol. We dissolved the pellet in 10 μl of TE and ligated 3 μl of this pUC8 DNA to 10 pmole of the synthetic terminator by incubating them overnight at 16° C. in 20 μl of buffer containing 800 units of T4 DNA ligase. We then transform *E. coli* K12 RR1ΔM15, a strain deposited and made part of the permanent stock culture collection of the Northern Regional Research Laboratory, Peoria, Ill., under the accession number NRRL B-15440, with 10 μl of the ligated DNA solution. We plate 0.1 ml of the transformed hosts onto TYAp100 medium containing 40 μg/ml XG and incubate them at 30° C. We then prepare a Kieser mini-prep of DNA from white colonies on the XG indicater plates and determine the structure of the recombinant DNA molecule by digestion with PvuII, BamHI and BglII.

The above procedure yields the plasmids pKC413 and pKC414. Plasmid pKC414 was found to comprise two transcription terminator sequences while plasmid pKC413 contained a single transcription terminator sequence. As shown in FIG. 2, the portable transcription terminator in plasmid pKC414 is flanked by BglII restriction sites so that it can be excised easily. The BglII sites are derived from the transcription terminator and are convenient since DNA cut by BqlII restriction endonucleases is self-ligatable and can also be ligated to BamHI, BclI or MboI generated ends.

EXAMPLE 3

In this example, we describe the effect of the present transcription terminator on transcription from the neomycin phosphotransferase promoter.

(1) Culture of *E. coli* K12 BE1041/pKC309 and Isolation of Plasmid pKC309

A. Culture

About 5 ml cultures of *E. coli* K12 BE1041/pKC309 (NRRL B-15827) were grown under selective conditions in TY media (1% tryptone, 0.5% yeast extract, 0.5% sodium chloride, pH 7.4) according to conventional microbiological procedures. The cells were spun in a table top centrifuge and the pellet resuspended in 1 ml of 0.3M sucrose, 25 mM EDTA (ethylene diaminetetracetate) and 25 mM Tris-HCl pH 8 (Solution I). After transfer to an Eppendorf tube the cells were centrifuged for about one minute and the pellet was resuspended in 0.5 ml of Solution I. About 50 μl of freshly made lysozyme (20 mg/ml in water) was added and the solution was incubated for 10 minutes at 37° C.

After the addition of 250 μl of freshly made lysis mix (2% sodium dodecyl sulfate and 0.3N NaOH), the cells were immediately and completely vortexed. The cells were then incubated for ten minutes at 70° C., cooled and added to 100 μl of phenol-Sevag (phenol-chloroform-isoamyl alcohol, 25:24:1). After the DNA was centrifuged for two minutes in an Eppendorf centrifuge the supernatant was decanted and transferred to another tube with 70 μl of unbuffered 3M sodium acetate and isopropanol to precipitate the DNA. This solution was incubated for five minutes at room temperature and then centrifuged for two minutes. The supernatant was gently and completely decanted to remove all the excess liquid.

The DNA precipitate was redissolved in 500 μl of TE (10 mM Tris-HCl, pH 8 and 1 mM EDTA) and 25 μl of 100 mM spermine HCl were added. This mixture was vortexed and then incubated for five minutes at room temperature before a five minute spin in an Eppendorf centrifuge. The supernatant was again completely decanted and discarded and the DNA reprecipitated with 1 ml of 75% ethanol, 0.3M sodium acetate, and 10 mM magnesium acetate. This solution was incubated for five minutes at room temperature and the DNA collected as above. The pellet was dissolved in 10 μl of TE for subsequent use as a cloning vehicle.

(2) Construction of Plasmid pKC345

A. BclI Digestion of Plasmid pKC309

About 10 μl of plasmid pKC309 DNA were digested in 1X BclI buffer (75 mM KCl, 10 mM Tris pH 7.4, 10 mM MgCl$_2$, and 10 mM DTT) in a total volume of 50 μl with 20 units (New England Biolabs) of BclI restriction endonuclease. The mixture was incubated at 50° C. for about 1½ hours. Next, 0.1 volume of 3M sodium acetate (NaOAc) was added which was followed by 3 volumes of 95% ethanol to precipitate the DNA. This ethanol precipitation was rapidly performed in a dry ice-isopropanol bath. The above procedure for an ethanol precipitation was performed throughout the following experiments unless otherwise indicated. The DNA precipitate was collected by centrifugation in an Eppendorf microfuge for 5 minutes. The DNA pellet was vacuum dried and then suspended in about 10 μl of water for subsequent ligation.

B. Isolation of Plasmid pEL103

1. Culture of *Streptomyces granuloruber* No. A39912.13/pEL103

A vegetative inoculum of *Streptomyces granuloruber* No. A39912.13/pEL103 (NRRL 12549) is conventionally prepared by growing the strain under submerged aerobic conditions in 50 ml of sterilized trypticase soy broth* at 35 g/L in deionized water.

*Trypticase soy broth is obtained from BBL Division, Becton-Dickinson & Company, Cockeysville, Md. 21030.

The trypticase soy broth inoculum is incubated for 48 hours at a temperature of 30° C. After incubation, about 10 ml of the inoculum is transferred to 500 ml of the sterilized broth and incubated for about 20 hours at 30° C. The pH is not adjusted. After incubation, the *Streptomyces granuloruber* No. A39912.13/pEL103 cells are ready for harvest and subsequent isolation of plasmid DNA.

2. Plasmid Isolation

About 12 g (wet wgt) of *Streptomyces granuloruber* No. A39912.13/pEL103 cells are centrifuged (10 minutes, 4° C., 10,000 rpm), washed in 10% glycerol, and then harvested by recentrifugation under the aforementioned conditions. About 50 ml of TES buffer (0.01M Tris(hydroxymethyl)aminoethane [Tris], 0.001M EDTA, 34% sucrose, pH 8) are added to the cells followed by about 0.25 g of lysozyme in 10 ml of 0.25M EDTA. After the mixture is incubated at 37° C. for about 15 minutes, about 0.5 ml of 10% Triton X-100 in TE buffer (0.01M Tris, .001M EDTA, pH 8) is added. The resultant mixture is then incubated at 65° C. for about 15 minutes. After the lysate is centrifuged (45 minutes, 4° C., 18,000 rpm), the supernatant is extracted four times with isoamyl alcohol and once with a chloroform-isoamyl alcohol solution (24:1). Next, 0.1 volume of 3M sodium acetate is added to the aqueous phase followed by 3 volumes of cold (−20° C.) 95% ethanol. The ethanol precipitation is rapidly performed in a dry ice-ethanol bath and the DNA precipitate collected by centrifugation (15 minutes, 4° C., 10,000 rpm). The precipitate is vacuum dried and then resuspended in 1.1 ml of STE buffer (0.01M Tris, 0.001M EDTA, 0.01M sodium chloride). Centrifugation (40 hours, 15° C., 35,000 rpm) using cesium chloride gradients with ethidium bromide, is carried out to purify the plasmid DNA. Following centrifugation, the desired plasmid pEL103 DNA band is removed and the ethidium bromide extracted by conventional procedures. After precipitation of the DNA in 3 volumes of ethanol, the isolated plasmid pEL103 DNA is dissolved in 1 ml of 10 fold diluted TE buffer and is then stored at −20° C.

3. BamHI Digestion of Plasmid pEL103 and Isolation of the ~2.9 kb Origin of Replication-Containing Fragment About 2 μg of plasmid pEL103 DNA is digested in 1X BamHI buffer (150 mM NaCl, 10 mM Tris pH 8, 10 mM MgCl$_2$) in a total volume of 50 μl with 16 units (New England Biolabs) of BamHI restriction endonuclease. The mixture is incubated at 37° C. for 30 minutes. The DNA is ethanol precipitated according to the method of Example 3(2A). Next, the DNA is electrophoresed on a 1% agarose gel until the desired ~2.9 kb BamHI fragment is separated from other fragments. The isolated ~2.9 kb fragment is removed from the gel, placed in a dialysis bag containing 0.5 ml Tris-acetate buffer supplemented with 0.5 μg/ml ethidium bromide and 100 μg/ml BSA and electroeluted at 50–100V until the DNA is eluted off the gel. Next, the buffer is removed and the DNA extracted with Sevag. The desired ~2.9 kb BamHI restriction fragment is ethanol precipitated and dissolved in TE buffer for subsequent ligation.

C. Construction of Plasmid pKC326 and *E. coli* K12 BE1041/pKC326

About 2 μg of BclI-digested plasmid pKC309 DNA and the ~2.9 kb BamHI Streptomyces origin of replication-containing fragment were ligated in 20 μl of 1X ligase buffer (50 mM Tris pH 7.8, 10 mM MgCl$_2$, 20 mM DTT, and 1 mM ATP) with 400 units of T4 DNA ligase overnight at 16° C. The DNA was ethanol precipitated, dried and redissolved in 5 μl TE for subsequent transformation.

Figure 4:
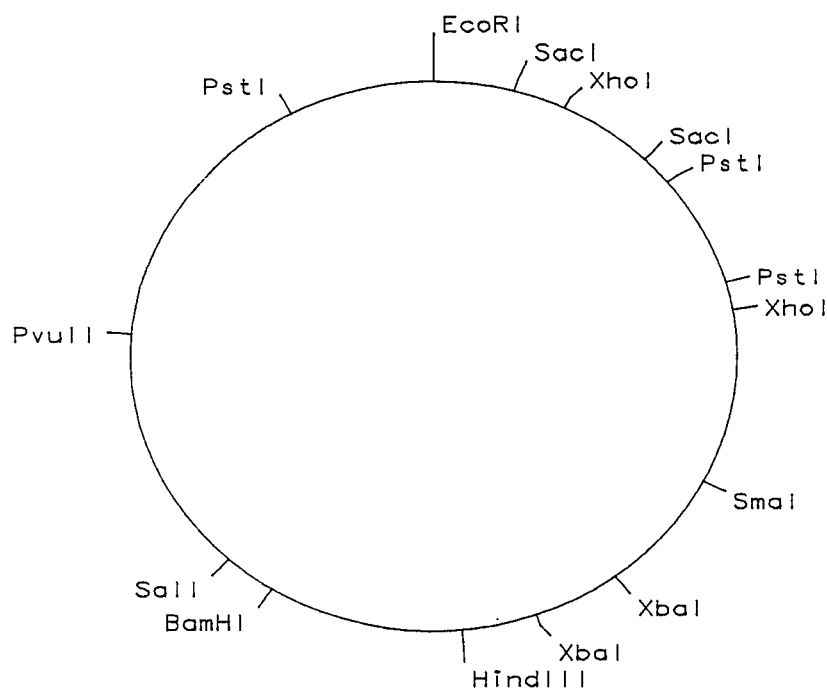
FIGS. 4–7 are respective restriction site maps of plasmid pKC326, pKC345, pKC354 and pKC356.

The resultant plasmid DNA was used to transform *E. coli* K12 BE1041 (NRRL B-15021) according to the procedure of Maniatis et al., 1982. The identity of the desired transformants was conventionally confirmed by screening for the acquisition of a PstI site. The resultant *E. coli* K12 BE1041/pKC326 transformants were conventionally cultured for subsequent production and isolation of plasmid pKC326. A restriction site and functional map of plasmid pKC326 is presented in FIG. 4 of the accompanying drawings.

D. Final Construction of Plasmid pKC345

1. BamHI Digestion of Plasmid pKC326

About 2 μg of plasmid pKC326 DNA was digested with BamHI restriction enzyme in substantial accordance with the teaching of Example 3(2B(3)), except that the digestion was carried out for 1 hour. The DNA was ethanol precipitated, dried and redissolved in 5 μl TE buffer for subsequent ligation to a thiostrepton resistance gene isolated from plasmid pIJ702.

2. BclI Digestion of Plasmid pIJ702 and Isolation of the ~1 kb Thiostrepton Resistance-Conferring Gene About 5 μg of plasmid pIJ702 DNA (ATCC 39155) (American Type Culture Collection, 12301 Parklawn Drive, Rockville, Md. 20852, U.S.A.) is digested with BclI restriction enzyme in substantial accordance with the teaching of Example 3(2A). The DNA is ethanol precipitated, dried and then dissolved in 5 μl TE. The DNA is electrophoresed on a 1% agarose gel until the desired ~1 kb BclI fragment is separated from other fragments. Whatman DEAE cellulose paper is placed in a slit prepared ahead of the desired DNA band and the DNA is electrophoresed onto the DEAE paper. The paper is washed with 1 ml of TE and the DNA is eluted with 400 μl of TE adjusted to 1M by the addition of an appropriate volume of NaCl. The eluted DNA is ethanol precipitated and finally dissolved in 5 μl of TE.

3. Ligation and Construction of *E. coli* K12 BE1041/pKC345

About 2 μg of BamHI-digested plasmid pKC326 DNA and ~5 μg of the ~1 kb BclI restriction fragment of plasmid pIJ702 DNA were ligated in substantial accordance with the teaching of Example 3(2C). After ethanol precipitation, the DNA was further digested with BamHI restriction enzyme to reduce the number of parental plasmids.

Figure 5:
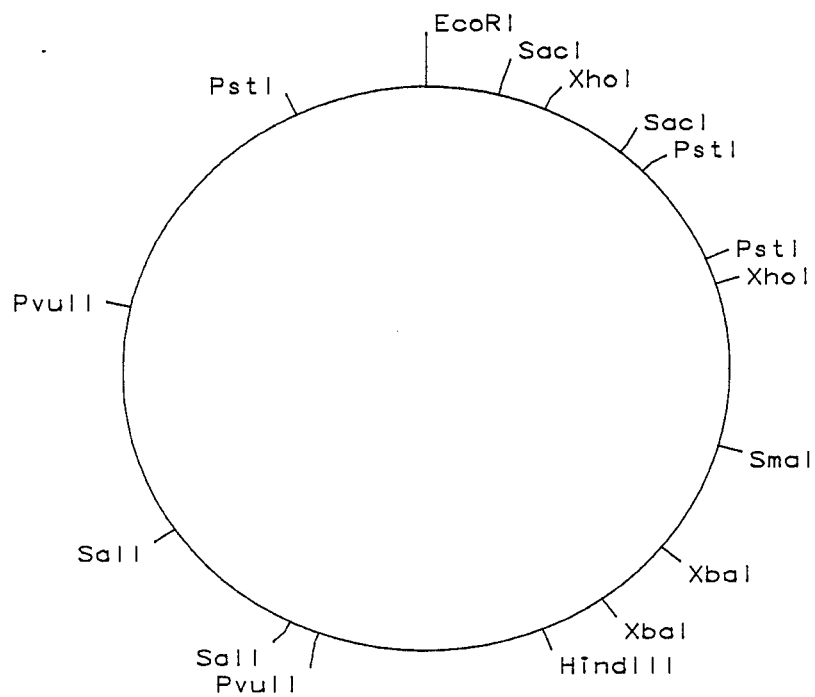

The resultant DNA was used to transform *E. coli* K12 BE1041 according to the procedure of Maniatis et al., 1982. The identity of the desired transformants was conventionally confirmed by screening for ampicillin resistance, tetracycline sensitivity and the acquisition of a SalI site. Transformed cells were conventionally cultured for subsequent production and isolation of plasmid pKC345. A restriction site and functional map of plasmid pKC345 is presented in FIG. 5 of the accompanying drawings.

(3) Construction of pKC354 and *E. coli* K12 BE1041/pKC354

A. AvaI Digestion of pKC322 and Isolation of the ~2.1 kb AvaI Restriction Fragment About 150 μg of plasmid pKC322 DNA (NRRL B-15829) were digested in 1X AvaI buffer (60 mM NaCl, 10 mM Tris pH 8, 10 mM DTT and 10 mM MgCl$_2$) in a total volume of 1 ml with 15 units (New England Biolabs) of AvaI restriction enzyme for 7 hours at 37° C. Another 20 units of AvaI restriction enzyme were added and the reaction was continued overnight. The resulting DNA, in the digestion buffer, was electrophoresed overnight at 50V on a 1% agarose gel in substantial accordance with the teaching of Maniatis et al., 1982.

The ~2.1 kb band was isolated from the gel and the DNA eluted from the gel in substantial accordance with the teaching of Example 3(2B(3)). The DNA was extracted twice with phenol and twice with Sevag (chloroform-isoamyl alcohol, 24:1). The ~2.1 kb AvaI fragment was purified using an Elutip-d column (Sohleioher and Schuell, Inc., Keene, N.H. 03431) and then precipitated with ethanol and redissolved in 20 μl TE. An equivalent method to purify DNA fragments can also be used whereby the DNA is electrophoresed on a 1% agarose gel until the desired fragment is separated from other fragments. Whatman DEAE cellulose paper is then placed in a slit prepared ahead of the desired DNA band and the DNA is electrophoresed onto the DEAE paper. The paper can then be washed with 1 ml TE and the DNA eluted with 400 μl TE which is adjusted to 1M by the addition of an appropriate volume of NaCl. The eluted DNA is ethanol precipitated and dissolved in 5 μl TE for subsequent ligation.

B. SacI Digestion of Plasmid pKC345

About 10 μg of plasmid pKC345 DNA were digested in 1X SacI buffer (10 mM MgCl₂, 10 mM Tris pH 7.4, and 10 mM DTT) in a total volume of 10 μl with 5 units (New England Biolabs) of SacI restriction endonuclease for 1 hour at 37° C. The reaction was terminated by increasing the temperature to 70° C. for 5 minutes.

C. Ligation to Construct Plasmid pKC354

About 5 μl each of the purified ~2.1 kb AvaI restriction fragment and the SacI-digested pKC345 were added to 2 μl of 10X T4 polymerase buffer (67 mM potassium acetate, 33 mM Tris-acetate pH 7.8, and 10 mM Magnesium acetate). Next, 1 μl of 20X deoxynucleotides (dATP, dGTP, dCTP, TTP; final concentration was 10 μM) was added and the volume adjusted to 20 μl with water. After 1 μl of T4 DNA polymerase was added the mixture was incubated at 37° C. for 5 minutes. This last step was repeated and then 2 μl of 50 mM EDTA were added and the reaction was terminated by increasing the temperature to 70° C. for 5 minutes. The DNA was extracted once with Sevag and after the volume was increased to 50 μl with water, the DNA was ethanol precipitated to remove the T4 polymerase salts. The DNA precipitate was suspended in 20 μl of T4 DNA ligase buffer supplemented with 400 units of T4 DNA ligase (NEB) and the ligation was run at 16° C. for 48 hours.

D. Transformation and Construction of E. coli K12 BE1041/pKC354

Figure 6:
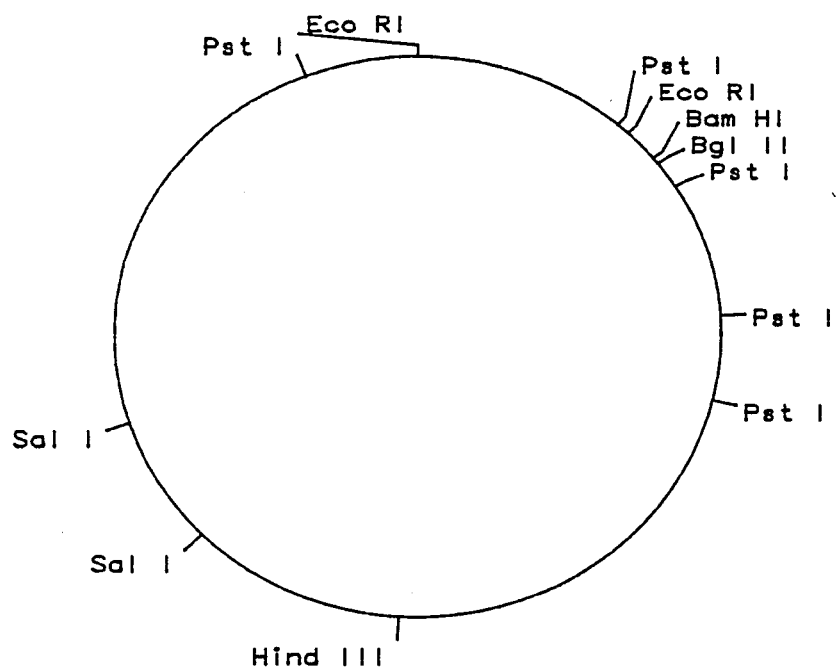

About 1 μl of the ligated DNA was used to transform *E. coli* K12 BE1041 according to the procedure of Maniatis et al., 1982. The transformants were conventionally screened using colony hybridization and a probe prepared by nick translating 2 μl of the purified ~2.1 kb AvaI restriction fragment. The identity of the desired transformants was conventionally confirmed by screening for ampicillin resistance and the acquisition of an EcoRI site, a BamHI site and a BglII site. Competent cells were conventionally cultured for subsequent production and isolation of plasmid pKC354. A restriction site and functional map of plasmid pKC354 is presented in FIG. 6 of the accompanying drawings.

(4) Construction of Plasmid pKC356 and E. coli K12 BE1041/pKC356

A EcoRI Digestion of Plasmid pKC354

Plasmid pKC356 was constructed by deleting an μ1.5 kb EcoRI fragment from plasmid pKC354. About 10 μg of pKC354 DNA were digested in 1X EcoRI buffer (100 mM Tris pH 7.5, 50 mM NaCl, and 10 mM MgCl₂) in a total volume of 20 μl with 24 units (New England Biolabs) of EcoRI restriction enzyme for 1 hour at 37° C. The resulting fragments were isolated by agarose gel electrophoresis and the μ11 kb EcoRI restriction fragment was extracted with phenol and Sevag, purified on an Elutip-d column and ethanol precipitated. The DNA precipitate was redissolved in 10 μl TE for subsequent ligation.

B. Ligation and Transformation

The resultant DNA was ligated in substantial accordance with the teaching of Example 3(2C) and incubated at 16° C. overnight to promote self-circularization. After incubation, the DNA was ethanol precipitated and dissolved in 10 μl TE.

Figure 7:
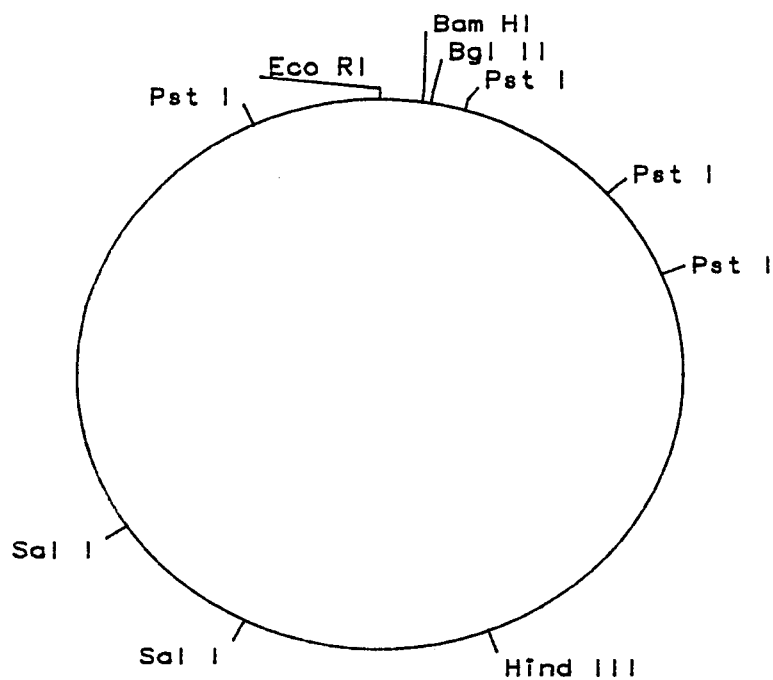

About 2 μl of the resultant DNA were used to transform *E. coli* K12 BE1041 in substantial accordance with the teaching of Maniatis et al., 1982. The identity of the desired transformants was conventionally confirmed by screening for ampicillin resistance and for the deletion of an EcoRI restriction site. Transformed cells were conventionally cultured for subsequent production and isolation of plasmid pKC356. A restriction site and functional map of plasmid pKC356 is presented in FIG. 7 of the accompanying drawings.

(5) Construction of Plasmid pKC388

Five μl of a stock solution of plasmid pKC7 (ATCC 37084) are digested for 1 hr at 37° C. in 50 μl of buffer with 50 units of PstI. A 10 μl aliquot is examined by gel electrophoresis to monitor the extent of digestion. The DNA solution is extracted with phenol:CHCl₃ (1:1) and precipitated with ethanol. The precipitated DNA is then digested with 25 units of EcoRI for 30 minutes at 37° C. in 50 μl of buffer.

One μg of plasmid pKC356 is also digested with EcoRI as set forth above. The two digests are then pooled and precipitated with ethanol. The pooled DNA is digested with 16 units of BglII in 100 μl of buffer for 40 min at 37° C. and then precipitated with ethanol. The pooled DNA comprising digests of pKC7 and pKC356 is ligated overnight with 400 units of T4 DNA ligase in 30 μl of buffer at 16° C. The *E. coli* strain BE1041 (NRRL B-15021) is transformed with 10 μl of the ligated DNA. The transformed hosts were incubated about 6 hours at 37° C. to allow expression of the plasmid genes. About 0.1 ml of the transformed *E. coli* K12 BE1041 is then plated on TYAp100Nm25 plates. Colonies which grow on these plates are isolated and grown overnight at 30° C. in TYAp100Nm25 broth. A Kieser mini-prep of DNA is done and the presence of the neomycin promoter is confirmed by digesting the DNA with HindIII in 15 μl of buffer for 2 hours at 37° C.

(6) Construction of plasmids pKC421 and pKC422

Figure 3:
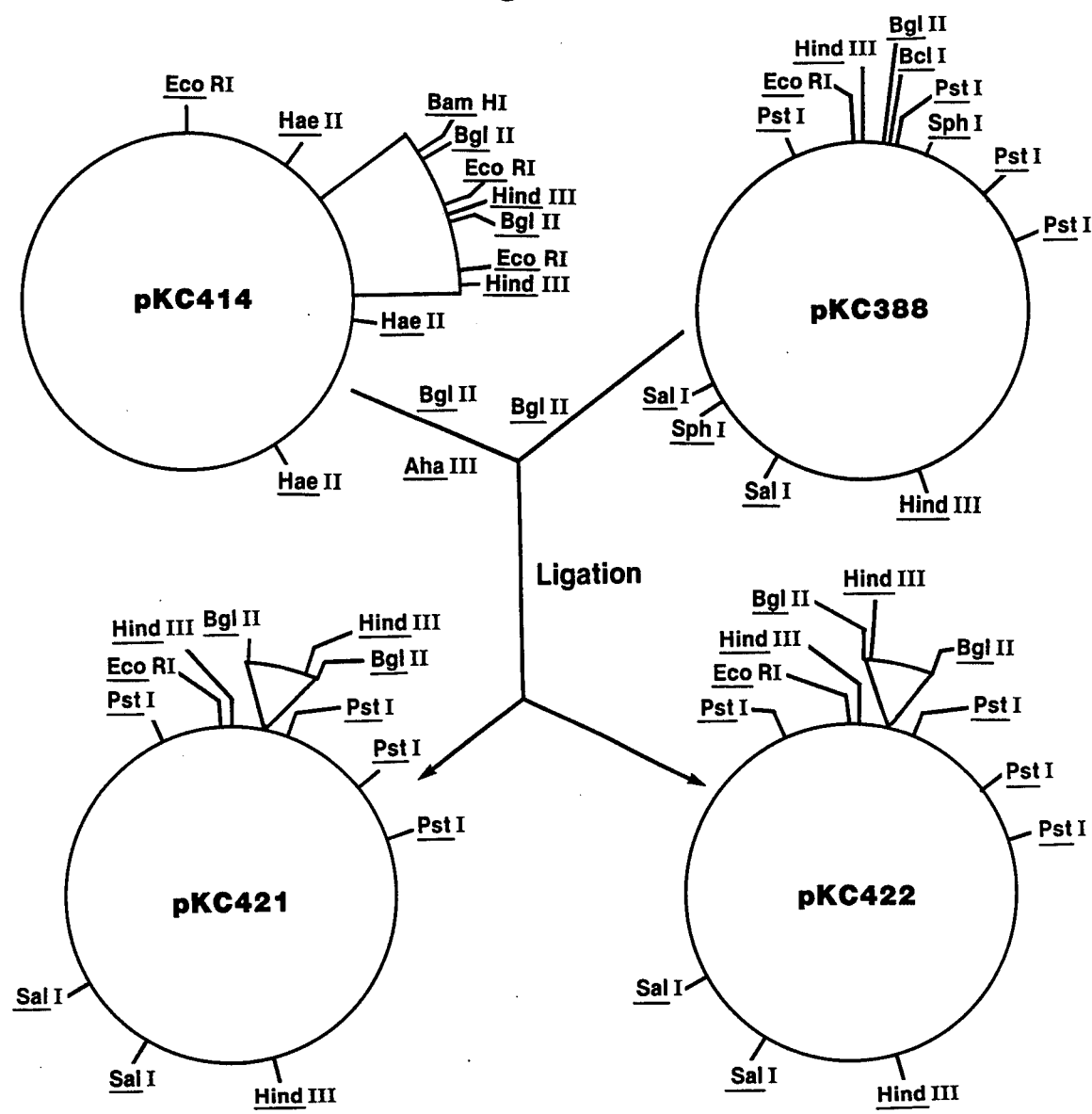
FIG. 3 is a schematic depiction of the construction of other expression-vectors comprising portable transcription terminators of this invention.

Referring now to FIG. 3, the BglII DNA sequence comprising the portable transcription terminator is excised from plasmid pKC414 and inserted into the unique BglII, site of plasmid pKC388 in two orientations. The plasmids are designated pKC421 and pKC422 and are produced as follows:

We digested about 1.8 μg of plasmid pKC414 with 6 units of AhaIII for 2 hr at 37° C. in 50 μl of buffer and precipitated the DNA with ethanol. We then digested the DNA with 8 units of BglII for 1 hr at 37° C. in 20 μl of buffer. We removed a 10 μl aliquot of this digested solution and precipitated it with ethanol.

We then digested about 5.2 μg of plasmid pKC388 with 12 units of BglII for 1 hour at 37° C. in 50 μl of buffer. We added 5 μl of 10×BAP buffer, 40 μl of H₂0O, and 0.25 units of IBI bacterial alkaline phosphatase and incubated this mixture at 70° C. for 1 hour. We extracted the mixture once with phenol and once with CHCl₃:isoamyl alcohol and then precipitated it with ethanol. We dissolved the precipitate in 11 μl of TE, added 2 μl of this DNA solution to the pKC414 digest and ligated the mixture overnight in 20 μl of buffer at 16° C. with 400 units of T4 DNA ligase. We then transformed *E. coli* K12 BE1041 with 10 μl of this recombinant DNA and allowed the transformant genes to express for 3 hr at 37° C. We plated 0.1 ml of the transformant culture on TYAp100 plates and incubated overnight at 37° C. We then did a Kieser DNA mini-prep using the transformed hosts and digested the isolated DNA with 20 units of both EcoRI and BglII to determine the plasmid structure.

Plasmid pKC388 contains a gene encoding neomycin phosphotransferase under the control of its own promoter. Plasmid pKC388 confers neomycin resistance (Neo®) to both E. coli and Streptomyces. When the portable transcription terminator of this invention was inserted into the BglII site of pKC388 (between the neomycin phosphotransferase promoter and the neomycin phosphotransferase gene) to produce plasmid pKC422 and when E. coli K12 BE1041 was transformed with the plasmid, the resulting transformants were sensitive to neomycin. The level of neomycin phosphotransferese was reduced by 50 percent when compared with the levels found in plasmid pKC388 transformed cells. Streptomyces ambofaciens transformed with pKC422 were also sensitive to neomycin and the level of neomycin phosphotransferase produced was reduced by as much as 88 percent.

The E. coli transformants of plasmid pKC421 (wherein the portable transcription terminator is oriented opposite to that in pKC422) were also sensitive to neomycin and the level of neomycin phosphotransferase activity was reduced by 38 percent. Streptomyces ambofaciens transformed with plasmid pKC421 were partially resistant to neomycin and the level of neomycin phosphotransferase activity was reduced by 37 percent. This change from neomycin resistance to neomycin sensitivity as a result of the insertion of the transcription terminator of this invention demonstrates the utility of this DNA sequence in reducing transcription.

We had not expected that the portable transcription terminator would function in the orientation found in plasmid pKC421. While not wishing to be bound by theory, the DNA sequence has a TTCTTT region after the stem structure that may function as the site of termination in plasmid pKC421. Furthermore, the stem structure of the transcription terminator may also include additional base pairing between residues 10–15 and 47–52.

EXAMPLE 4

In this example, we demonstrate that SmaI restriction of the DNA sequence of this invention prevents its use as a transcription terminator. This loss of function as a result of SmaI restriction is also evidence that the stem and loop structure downstream of the SmaI site is related to the transcription termination effect of the DNA sequence.

We designed our portable transcription terminator so that SmaI restriction would delete a section of the DNA and thereby prevent the formation of a stem structure and eliminate the transcription terminator function (see FIG. 1). To test this theory, we digest plasmids pKC421 and pKC422 with SmaI and then religate to delete residues 22 through 40. We verify the DNA sequences by the method of Messing, supra. These plasmids are designated pKC485 and pKC486. Both E. coli and Streptomyces ambofaciens transformed with these plasmids are resistant to neomycin and exhibited neomycin phosphotransferase activity, thereby confirming the elimination of the transcription termination function.

EXAMPLE 5

Various functional derivatives of the transcription terminator can also be used in accordance with the present disclosure. These derivative sequences are shown below and can be constructed in substantial accordance with the teaching of Example 1.

```
5' AATTCCCGGGTGGGTATTTCCCACCCGGGTAGTTTTTGTT 3'
   ||||||||||||||||||||||||||||||||||||||||
3' TTAAGGGCCCACCCATAAAGGGTGGGCCCATCAAAAACAA 5'

5' CCCGGGTGGGTATTTCCCACCCGGGTAGTTTTT 3'
   |||||||||||||||||||||||||||||||||
3' GGGCCCACCCATAAAGGGTGGGCCCATCAAAAA 5'
```

The above defined sequences function as transcription terminators and can be incorporated into vectors and used in substantial accordance with the foregoing examples.

EXAMPLE 6

The transcription terminator sequences defined in Examples 1 and 6 are transcribed in vivo to form mRNA. These specific mRNA sequences which further comprise the present invention include

GAAAGCUUUCAAAGAAUUCCCGGGUGGGUAUU

UCCCACCCGGGUAGUUUUUGUU, AAUUCCCGGGU

GGGUAUUUCCCACCCGGGUAGUUUUUGUU, AND

CCCGGGUGGGUAUUUCCCACCCGGGUAGUUUUU wherein
A is riboadenyl
G is riboguanyl,
C is ribocytosyl and
U is ribouracyl.

The above defined sequences are produced in vivo or can be conventionally synthesized in accordance with known methods.

While we have presented a number of embodiments of this invention, it is apparent that our basic construction can be altered to provide other embodiments which utilize the processes and compositions of this invention. Therefore, it will be appreciated that the scope of this invention is in no way limited by the specific embodiments which have been presented by way of example.

We claim:

1. A DNA sequence selected from the group consisting of:

```
5' GAAAGCTTTCAAAGAATTCCCGGGTGGGTATT-
3' CTTTCGAAAGTTTCTTAAGGGCCCACCCATAA-

TCCCACCCGGGTAGTTTTTGTTAACTAAGATCT 3'
AGGGTGGGCCCATCAAAAACAATTGATTCTAGA 4',

5' AATTCCCGGGTGGGTATTT-
3' TTAAGGGCCCACCCATAAA-

CCCACCCGGGTAGTTTTTGTT 3'
GGGTGGGCCCATCAAAAACAA 5',
```

-continued and

5' CCCGGGTGGGTATTTCCCACCCGGGTAGTTTTT 3'
3' GGGCCCACCCATAAAGGGTGGGCCCATCAAAAA 5' wherein
A is deoxyodenyl
G is deoxyguanyl,
C is deoxycytosyl and
T is thymidyl.

2. A recombinant DNA molecule comprising a recombinant DNA and a DNA sequence selected from the group consisting of

5' GAAAGCTTTCAAAGAATTCCCGGGTGGGTATT-
3' CTTTCGAAAGTTTCTTAAGGGCCCACCCATAA-

TCCCACCCGGGTAGTTTTTGTTAACTAAGATCT 3'
AGGGTGGGCCCATCAAAAACAATTGATTCTAGA 4',

5' AATTCCCGGGTGGGTATTT-
3' TTAAGGGCCCACCCATAAA-

CCCACCCGGGTAGTTTTTGTT 3'
GGGTGGGCCCATCAAAAACAA 5', and

5' CCCGGGTGGGTATTTCCCACCCGGGTAGTTTTT 3'
3' GGGCCCACCCATAAAGGGTGGGCCCATCAAAAA 5' wherein
A is deoxyodenyl
G is deoxyguanyl,
C is deoxycytosyl and
T is thymidyl,
said DNA sequence being located in said recombinant DNA in either orientation.

3. The recombinant DNA molecule of claim 2 wherein said molecule is selected form the group consisting of pKC413, pKC414, pKC421 and pKC422.

4. The recombinant DNA molecule of claim 2 wherein at least one of said DNA sequences is located downstream of the stop codon of a DNA sequence in said molecule that codes for a desired polypeptide.

5. The recombinant DNA molecule of claim 2 wherein at least one of said DNA sequences is located upstream of a promoter sequence in such molecule that controls the expression of a DNA sequence that codes for a desired polypeptide.

6. The recombinant DNA molecule of claim 4 wherein at least one of said DNA sequences is located in said molecule upstream of a promoter sequence that controls the expression of the DNA sequence that codes for the desired polypeptide.

7. The recombinant DNA molecule of claim 5 wherein said promoter is selected from the group consisting of the trp promoter, the lac promoter, the TAC promoter, the lpp promoter, a promoter of bacteriophage phage λ, the β-lactamase promoter, the Bacillus veg promoter, the Staphylococcus nuclease promoter, a promoter that controls the expession of prokaryotic, eukaryotic and viral genes.

8. The recombinant DNA molecule of claim 6 wherein said promoter is selected from the group consisting of the trp promoter, the lac promoter, the TAC promoter, the lpp promoter, a promoter of bacteriophage phage λ, the β-lactamase promoter, the Bacillus veg promoter, the Staphylococcus nuclease promoter, a promoter that controls the expression of prokaryotic, eukaryotic and viral genes.

9. A microbial host transformed with a recombinant DNA molecule of claim 2.

10. A microbial host transformed with a recombinant DNA molecule of claim 3.

11. A microbial host transformed with a recombinant DNA molecule of claim 4.

12. A microbial host transormed with a recombinant DNA molecule of claim 5.

13. A microbial host transformed with a recombinant DNA molecule of claim 6.

14. The microbial host according to claim 9, wherein the host is selected from the group consisting of E. coli, Bacillus, Streptomyces, and yeast.

15. The microbial host of claim 10 wherein the host is selected from the group consisting of E. coli, Bacillus, Streptomyces, and yeast.

16. The microbial host of claim 15 wherein the host selected from the group consisting of E. coli, Bacillus, Streptomyces, and yeast.

17. The microbial host of claim 12 wherein the host is selected from the group consisting of E. coli, Bacillus, Streptomyces, and yeast.

18. The microbial host of claim 13 wherein the untransformed host is selected from the group consisting of E. coli, Bacillus, Streptomyces, and yeast.

19. A method of terminating transcription of a DNA sequence comprising the step of inserting a DNA sequence of claim 1 downstream of the DNA sequence whose transcription is to be terminated.

20. A method of terminating transcription of a DNA sequence comprising the step of inserting a DNA sequence of claim 1 upstream of the DNA sequence whose transcription is to be terminated.

21. A method for reducing tanscription of a DNA sequence in a Streptomyces host cell that comprises placing a transcription terminator of claim 1 between the promoter driving transcription and the DNA sequence whose transcription is to be reduced.

22. The method of claim 21, wherein said transcription terminator is placed in a recombinant DNA expression vector.

* * * * *

UNITED STATES PATENT AND TRADEMARK OFFICE
CERTIFICATE OF CORRECTION

PATENT NO. : 4,710,464

DATED : December 1, 1987

INVENTOR(S) : Ramamoorthy Belagaje, Stuart A. Kuhstoss and R. Nagaraja Rao.

It is certified that error appears in the above-identified patent and that said Letters Patent is hereby corrected as shown below:

Column 4, line 6, insert the word --selected-- after the words "should be"

Column 12, line 55, "Sohleioher" should read --Schleicher--.

Column 13, line 59, "µ11 kb EcoRI" should read --∿11 kb EcoRI--.

Column 14, line 58, "$H_{20}O$" should read --$H_2O$--.

Column 15, line 10, "(Neo®)" should read --(Neo$^R$)--.

Column 16, line 63, "4'" should read --5'--.

Column 17, line 39, "form" should read --from--.

Column 18, line 10, "Ipp" should read --lpp--.

Column 18, line 21, "transormed" should read --transformed--.

Column 18, line 32, "15" should read --11--.

Signed and Sealed this

Nineteenth Day of November, 1991

Attest:

HARRY F. MANBECK, JR.

*Attesting Officer*   *Commissioner of Patents and Trademarks*